United States Patent [19]
Hall

[11] Patent Number: 5,746,988
[45] Date of Patent: May 5, 1998

[54] APPARATUS FOR PROCESSING BIO-HARZARDOUS WASTE

[75] Inventor: John L. Hall, Tracy, Calif.

[73] Assignees: Darlene Hall, Edmonds, Wash.; Wilburn E. Hall, Newport, Oreg.; Vern W. Hall, Kodiak, Ak.; part interest to each

[21] Appl. No.: 562,508

[22] Filed: Nov. 24, 1995

[51] Int. Cl.$^6$ .................................................. A61L 2/00
[52] U.S. Cl. .................... 422/292; 422/295; 422/299; 422/300; 422/26; 100/70 R; 100/73
[58] Field of Search ................ 422/26, 292, 295, 422/299, 300, 297; 100/70 R, 71, 73–75

[56] References Cited

U.S. PATENT DOCUMENTS

| | | | |
|---|---|---|---|
| 4,374,491 | 2/1983 | Stortroen et al. | 100/73 |
| 4,694,846 | 9/1987 | Bouchard | 134/97 |
| 5,084,250 | 1/1992 | Hall | 422/292 |
| 5,294,412 | 3/1994 | Orlando | 422/295 |
| 5,389,347 | 2/1995 | Hall | 422/307 |

*Primary Examiner*—Christopher Kim
*Attorney, Agent, or Firm*—Harris Zimmerman

[57] ABSTRACT

Infectious wastes from hospitals or other sources are sterilized in a chamber which is pivotable between a waste loading orientation, a sterilizing orientation and a waste dumping orientation. The chamber is attached to a framework by first and second pairs of pivot arms which are coupled to the sides of the chamber at spaced apart locations. An actuator swings the first arms upward to bring the chamber to the loading orientation and swings the arms downward to turn the chamber to the dumping orientation. The pivot arm arrangement causes the chamber as a whole to lower as it turns towards the loading orientation and to rise as it turns towards the dumping orientation. This reduces the amount of lifting of materials that is required during loading operations while also providing adequate clearance under the chamber for dumping operations. In one form, the chamber is translatable horizontally between a waste sterilizing location at which a chamber sealing door is situated and a loading and dumping location situated over a waste compactor intake compartment. A plurality of the chambers may be in side-by-side relationship and be loaded, operated and dumped at different times thereby enabling a continuous inflow of waste material.

20 Claims, 5 Drawing Sheets

APPARATUS FOR PROCESSING BIO-HARZARDOUS WASTE

TECHNICAL FIELD

This invention relates to the processing of infectious wastes from hospitals, medical clinics and the like and more particularly to waste sterilizing apparatus of the kind having a sterilizing chamber which pivots between a waste loading orientation and a waste dumping oriention.

BACKGROUND OF THE INVENTION

Potentially infectious wastes from medical facilities or other sources must be sterilized prior to disposal of the wastes at a landfill or other disposal site. An advantageous type of waste processor for this purpose has a sterilizing chamber for receiving the infectious waste and a door which enables sealing of the chamber. Pressurized steam is directed into the sealed chamber to destroy bio-hazardous organisms. Subsequently the chamber is unsealed and turned to a partially inverted orientation to dump the processed waste into a compactor which is situated below the chamber. The compactor then forces the wastes into an adjacent waste carrier for transport to a dump site.

The sterilizing chamber of the above described apparatus extends horizontally when at its loading orientation and the chamber opening faces in a horizontal direction. Bags of waste must be placed within the chamber including at locations which are away from the access opening of the chamber. Loading of bags of waste into the chamber, either manually or by means of mechanical devices such as conveyer belts, lifts or the the like, would be more convenient if the bags could simply be dropped into the chamber. This would require that the chamber have an at least partially upright orientation during the loading operation.

Pivoting the sterilizing chamber of the above described prior apparatus into a partially upright position would have an adverse effect on another aspect of the loading operation. The prior chamber turns about a single horizontal pivot axis that is located more or less midway between the front and back of the chamber. Consequently the access opening would be raised as the chamber was turned towards an upright position. It is preferable that the elevation of the chamber opening be kept to a minimum in order to miminize the amount of lifting that is needed during the loading operation.

This problem cannot be resolved by simply lowering the location of the above described prior chamber relative to the underlying surface or structure as some elevation of the chamber is needed to enable the dumping operation. The front end of the chamber is lowered as the chamber pivots towards its dumping orientation and space must be provided below the chamber to accommodate to this movement. Additional space is needed to allow the dumping to occur.

The present invention is directed to overcoming one or more of the problems discussed above.

SUMMARY OF THE INVENTION

In one aspect, the present invention provides a waste sterilizer having a framework supporting a receptacle that forms a chamber in which wastes are sterilized. The receptacle has an opening for receiving wastes and is pivotable between a loading orientation at which wastes are retained in the receptacle and a waste dumping orientation at which wastes are released from the receptacle through the opening. The receptacle is coupled to the framework by at least a first pivot arm and a second pivot arm each of which is pivotable relative to the framework and pivotable relative to the receptacle. The first pivot arm is coupled to the receptacle by a first pivot coupling and the second pivot arm is coupled to the receptacle by a second pivot coupling which is closer to the access opening of the receptacle than the first pivot coupling.

In another aspect of the invention the framework is a movable framework supported by a fixed framework, the movable framework and receptacle being translatable in a horizontal direction between a waste sterilizing position and a loading and dumping position. A door, proportioned for closing the receptacle, is attached to the fixed frame framework at the waste sterilizing position and is movable towards the receptacle opening and away therefrom.

In another aspect of the invention a plurality of the waste receptacles are disposed in side-by-side relationship each being coupled to the framework by a separate pair of the first pivot arms and a separate pair of the second pivot arms. A plurality of extendible and contractible actuators are connected between the framework and at least one of the first pivot arms at each receptacle. The actuators have a stroke sufficiently long to turn the receptacles between loading orientations at which the receptacle openings face at least partially in an upward direction and a dumping orientation at which the openings face at least partially downward. A plurality of doors are attached to the framework with each door being adjacent to a separate one of the receptacles. The doors are movable to close and open the access opening of the adjacent receptacle when the receptacle is at an intermediate orientation at which the opening of the receptacle faces in a horizontal direction. A plurality of waste receiving hoppers are disposed above the receptacles in spaced apart relationship therewith. A waste guiding chute extends between each hopper and the underlying receptacle, the chutes being extendible towards the receptacles and retractable therefrom.

In still another aspect the invention provides a waste sterilizer having a framework and a receptacle forming a sterilization chamber. A pair of first pivot arms are disposed at opposite sides of the receptacle and a pair of second pivot arms are also disposed at the same opposite sides of the receptacle. A pair of first pivot couplings couple the first pivot arms to said receptacle and are pivotable about a first pivot axis which is spaced apart from the front and back ends of the receptacle. A pair of second pivot couplings couple the second pivot arms to said receptacle and are pivotable about a second pivot axis which is parallel to the first pivot axis and which is closer to the front end of the receptacle than the first pivot axis. A pair of third pivot couplings couple the first pivot arms to the framework and are pivotable about a third pivot axis which is parallel to said first pivot axis. A pair of fourth pivot couplings couple the second pivot arms to the framework and are pivotable about a fourth pivot axis which is parallel to the first pivot axis and which is horizontally and vertically spaced apart from the third pivot axis. An actuator is coupled to at least one of the first pivot arms and acts to pivot the arm about the third pivot axis. A door is supported by the framework and is movable towards the receptacle and away therefrom, the door being proportioned to close the opening when the receptacle is pivoted into an orientation at which the opening faces in a horizontal direction.

The invention facilitates waste loading and waste dumping operations at a bio-hazardous waste sterilizer of the above described type. The waste receiving receptacle is supported by two pairs of spaced apart pivot arms in a manner which causes the receptacle as a whole to be lowered as it is turned towards an upwardly facing waste loading orientation and to be raised as it is turned towards a downwardly facing dumping orientation. The amount of lifting of wastes that is required during loading is reduced as the receptacle is in its lowered condition at that time. Ample clearance space for dumping of wastes is provided as the receptacle is in its raised condition during the dumping stage. In one form of the invention the framework to which the receptacle is attached by the pivot arms is a movable framework that is translatable along a fixed framework between a waste sterilizing location and an adjacent loading and dumping location. A movable pressure sealing door at the waste sterilizing location enables sealing of the receptacle during the sterilization stage of operation. The movable framework enables repeated loadings of successive batches of waste without requiring operation of a pressure sealing door during each such loading. The movable framework and receptacle also enables direct deposit of harmless wastes in the area where sterilized wastes are dumped from the receptacle as the receptacle may be traveled away from the loading and dumping location to enable the operation. Another embodiment of the invention enables high capacity waste sterilization operations on a more efficient basis by utilizing a series of the waste receptacles disposed in a side by side arrangement. A separate feed hopper is disposed above each such receptacle and a retractable chute under each hopper directs wastes to the underlying receptacle. The plural receptacles enable loading of new wastes to continue while one or more prior batches of waste are being sterilized. A translatable secondary conveyer belt enables feeding of the plural hopper with a single primary conveyer belt.

The invention, together with further aspects and advantages thereof, may be further understood by reference to the following description of preferred embodiments and by reference to the accompanying drawings.

DETAILED DESCRIPTION OF THE PREFERRED EMBODIMENTS

Figure 1:
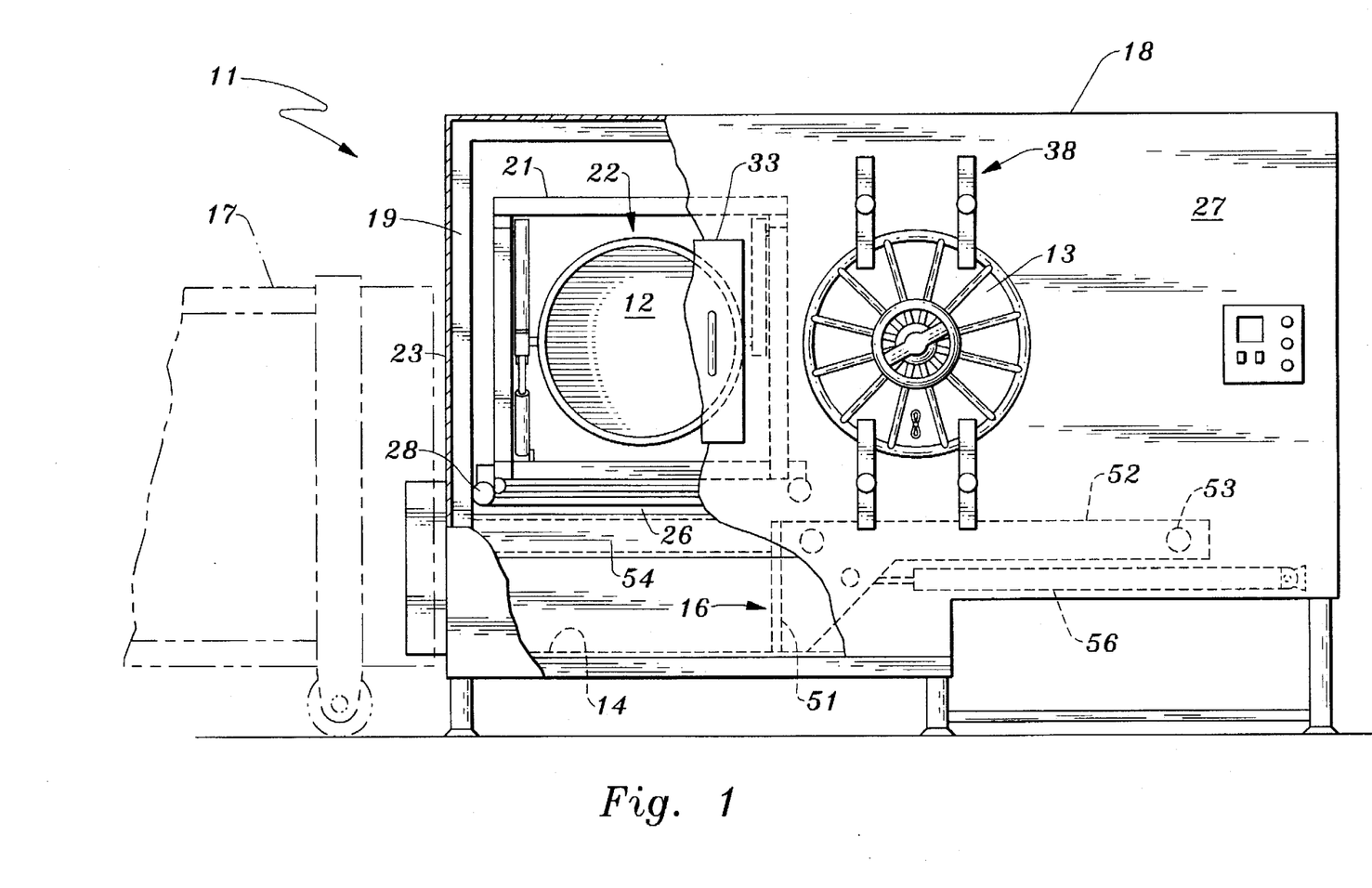
FIG. 1 is a broken out front elevation view of a waste sterilizer and compactor embodying the invention.

Referring initially to FIG. 1 of the drawings, a waste sterilizer and compactor 11 in accordance with this embodiment of the invention is typically located at a hospital, medical clinic or the like where bio-hazardous wastes such as used hypodermic needles, bandages, tissues and specimen containers for example, are produced. The wastes are initially deposited in waste containers which are lined with plastic bags. The plastic bags are subsequently transferred to a waste receptacle 12 within the sterilizer and compactor 11. Waste receptacle 12 can be sealed by a pressure sealing door 13, in a manner which will hereinafter be described in more detail, to enable sterilization of the wastes by subjecting the plastic bags to pressurized steam for a period sufficient to destroy infectious viruses and bacteria. The sterilized wastes are then dumped from receptacle 12 into a compactor chamber 14 in a manner which will also be further described. A compactor ram 16 then urges the processed wastes into a waste receiver 17 that is situated adjacent to one end of the sterilizer and compactor 11. When filled, the receiver 17 is transported to a dump site for disposal of the wastes.

Figure 2:
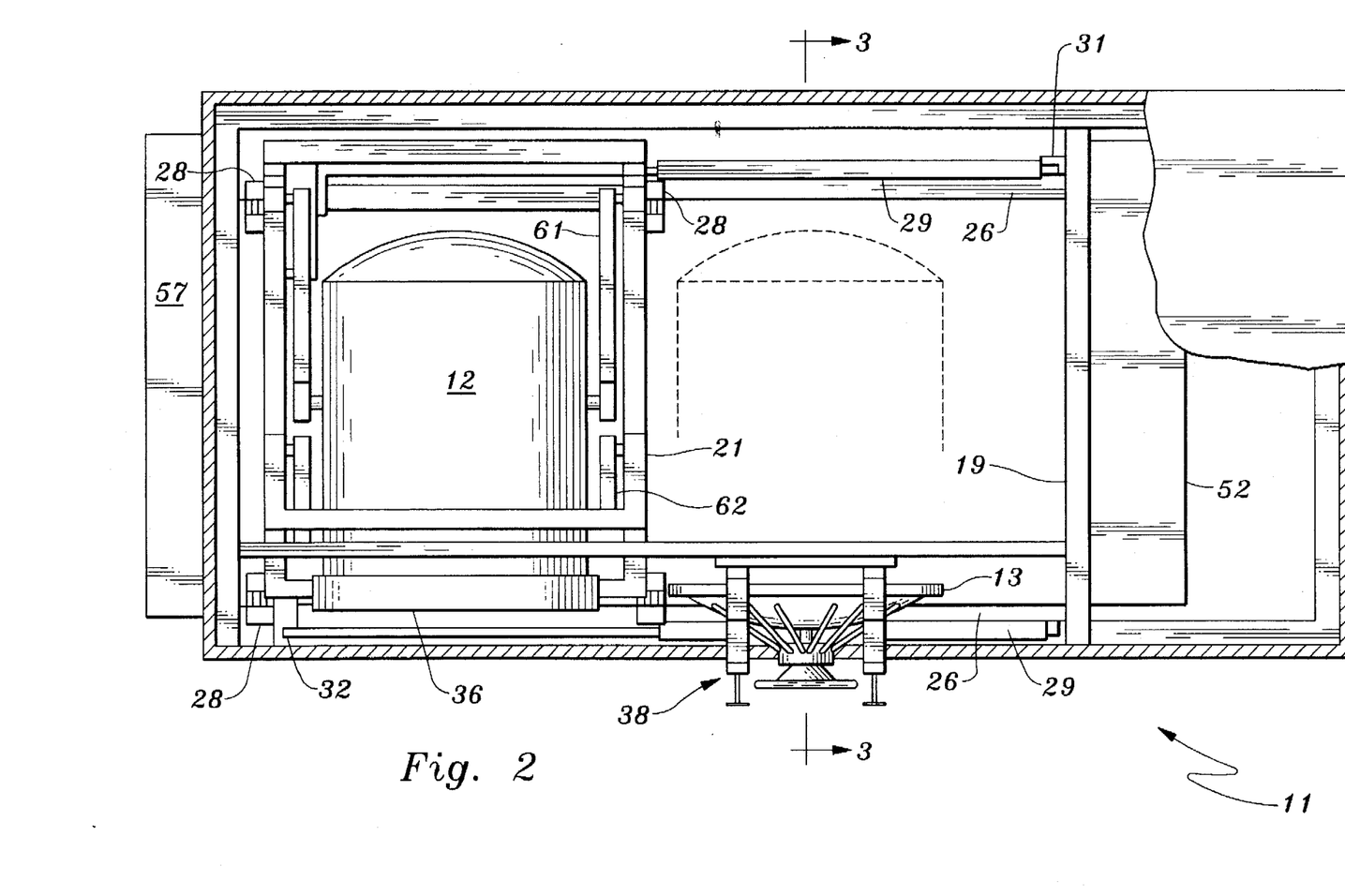
FIG. 2 is a broken out top view of the apparatus of FIG. 1.
Figure 3:
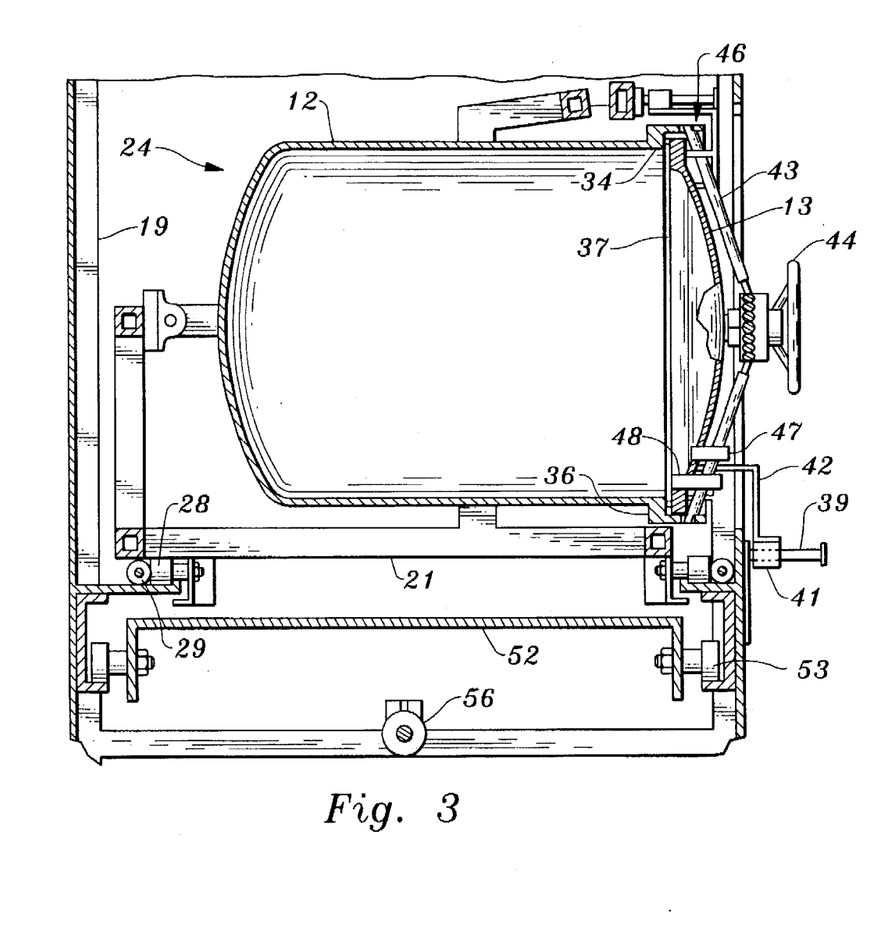
FIG. 3 is a cross section view of the apparatus of the preceding figures taken along line 3—3 of FIG. 2 except that a movable waste receiver and its carrier framework are shown at different locations along their path of travel in FIGS. 2 and 3.

Referring jointly to FIGS. 1, 2 and 3, the waste receptacle 12 is situated within a housing 18 which is supported by a fixed framework 19. The receptacle 12 is carried by a movable inner framework 21 which is translatable between a first location 22 at which the receptacle is in proximity to one end wall 23 of housing 18 and over the open topped compactor chamber 14 as shown in FIGS. 1 and 2 and a second location 24 at which the receptacle is behind the pressure sealing door 13 as shown in FIG. 3.

Referring again to FIGS. 1, 2 and 3 in conjunction, this travel of the receptacle 12 is provided for by spaced apart parallel rails 26 which extend horizontally within housing 18 in parallel relationship with the front wall 27 of the housing and which support the movable inner framework 21. Roller wheels 28 at the bottom of the movable framework 21 ride on the rails 26. One of a pair of extensible and contractable actuators 29 is adjacent to each of the rails 26 and extends in parallel relationship with the rails, one end of each actuator being coupled to the fixed framework 19 by a pivot coupling 31 and the other end of the actuator being coupled to the movable framework 21 by another pivot coupling 32. The actuators 29 are hydraulic cylinders in this example of the invention but other forms of translating mechanism can be used or the movable framework 21 and receptacle 12 can be manually translated in other embodiments of the invention.

The first location 22 of the receptacle 12, at which it is over compactor chamber 14, is the position at which wastes are loaded into the receptacle and also the position at which sterilized wastes are dumped from the receptacle into the compactor. A door 33 at the front wall 27 of housing 18 is situated above compactor chamber 14 and provides access for depositing bags of waste in the receptacle 12. Non-infectious wastes, which do not require sterilization, can be deposited directly in the compactor chamber 14 by traveling the movable framework 21 and receptacle 12 to their alternate position 24 behind the pressure sealing door 13.

The second position 24 of the receptacle 12, behind pressure sealing door 13, is the waste sterilizing position. The receptacle 12 of this embodiment is cylindrical and has a circular opening 34 at its front end that is encircled by a flange 36 which extends radially outward for a short distance and then axially outward for a somewhat greater distance.

Flange 36 is proportioned to enable seating of the rim of the pressure sealing door 13 against the radially directed portion of the flange. This compresses a circular seal 37 formed of resilient material between the door 13 and flange 36.

The previously described lateral travel of receptacle 12 between its two alternate locations is provided for by attaching door 13 to the fixed framework 19 in a manner which enables it to be drawn out of receptacle flange 36 and re-entered into the flange by axial movement of the door. In particular, door 13 is attached to the fixed framework 19 by four linear slide bearings 38 of which two are situated above the door and two are below the door. Each such slide bearing 38 includes a rod 39 which extends outward from the framework 19 and a slidable collar 41 through which the rod extends. Angled brackets 42 secure door 13 to the slidable collars 41.

The pressure sealing door 13 of this embodiment is of the known type which has radially directed latching arms 43 that are translatable by turning of an actuator wheel 44 and which engage in openings 46 in receptacle flange 36 with a wedging action that causes the door to exert pressure against seal 37. The detailed construction of such doors 13, commonly used to seal openings in the bulkheads of ships, is known to the art. Other forms of pressure sealing door, including hinge mounted doors, may also be used to seal the receptacle 12.

Sterilizing of the contents of receptacle 12 is effected by admitting pressurized steam into the sealed receptacle through a first fitting 47 at door 13. Steam condensate is withdrawn from the receptacle 12 through a second fitting 48 situated at the base of the door 13.

The steam supply and condensate pumping system may be of the known form. Similarly, hydraulic circuits including valves for controlling the hydraulic cylinder actuators of the waste sterilizer and compactor 11 may be of known forms. Examples of components for this purpose are described in prior U.S. Pat. No. 5,084,250 which patent is herein incorporated by reference.

Compactor 16 includes a translatable ram 49 having an upright plate 51 that extends across the compactor chamber 14 and which is joined to an inverted channel shaped and horizontally directed member 52 that extends away from the chamber below the path of travel of the receptacle 12. The ram 49 rides on roller wheels 53 which are situated at each side of member 52 and which travel within channel members 54 that extend along the path of travel of the ram. An extensible and contractible actuator 56, which is another hydraulic cylinder in this example, extends below member 52 in parallel relationship with the member and is pivotally coupled to the ram 49 and to fixed framework 19. Actuator 56 is proportioned to travel the ram 49 along compactor chamber 14, through a frame 57 that protrudes from housing end wall 23 into a conforming opening 58 in waste receiver 17 and to travel the ram a short distance further into the waste receiver itself. Thus the ram 49 transfers wastes which have been deposited in chamber 14 into the waste receiver 17.

FIGS. 1 to 3 depict the waste receptacle 12 in a horizontal orientation at which the opening 34 of the receptacle faces in a horizontal direction. This is the orientation at which it engages with pressure sealing door 13 and at which the sterilization operation is conducted. To facilitate loading the receptacle is pivoted into another orientation, shown in FIG. 4E, at which the receptacle opening faces partially in an upward direction. At this orientation bags of waste can simply be dropped into receptacle 12. The receptacle 12 is pivoted to still another orientation, shown in FIG. 4D, in order to dump sterilized wastes from the receptacle. At the dumping orientation the receptacle opening faces partially in a downward direction.

Referring jointly to FIGS. 4A to 4E, the receptacle 12 is supported by the movable frame 21 in a manner which causes the receptacle as a whole to be lowered as it turns towards the loading orientation and to rise as it turns towards the dumping orientation. This reduces the amount of lifting of bags of waste that is required during the loading operation while providing adequate dumping space during the dumping operation. The receptacle 12 may be at a lower elevation during the sterilizing operation than would otherwise be necessary. This facilitates operation of the pressure sealing door.

These results are brought about by coupling the receptacle 12 to the movable frame 21 by both a first pair of pivot arms 61 and a second pair of pivot arms 62 in a manner which causes the receptacle to pivot about two spaced apart parallel pivot axes 63 and 64 rather than about a single pivot axis. The pivot arms 61 and 62 of each pair are at opposite sides of the receptacle 12. The first pivot axis 63 is defined by first pivot couplings 66 which couple ends of the first pivot arms 61 to the receptacle 12 at corresponding locations on opposite sides of the receptacle. Second pivot couplings 67 couple ends of the second pivot arms to the receptacle 12 at corresponding locations on opposite sides of the receptacle to define the second pivot axis 64. The first pivot couplings 66 and thus the first pivot axis are spaced apart from both ends of the receptacle 12 and are preferably midway between the receptacle opening 34 and the back of the receptacle. Second pivot couplings 67 and thus the second pivot axis 64 are at locations which are closer to the opening 34 of the receptacle 12 than the locations of the first pivot couplings 66 and are preferably at locations which are spaced from the opening about one third of the spacing of the first pivot couplings from the opening.

Figure 4A:
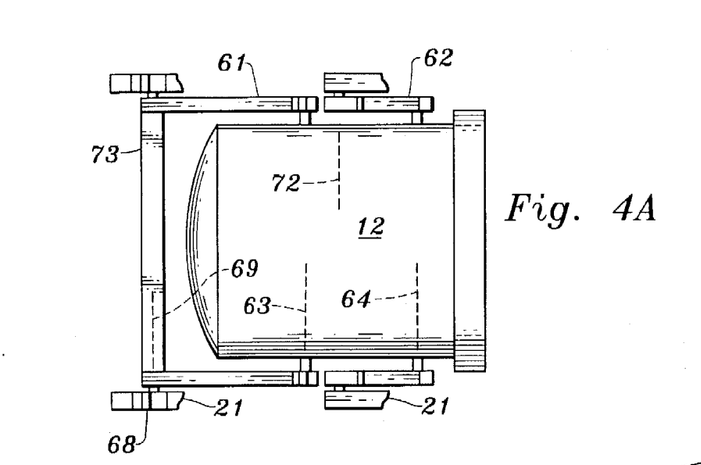
FIG. 4A is a top view of a pivotable waste recepacle which is a component of the apparatus of the preceeding figures and includes certain other components which are adjacent to the waste receptacle.
Figure 4B:
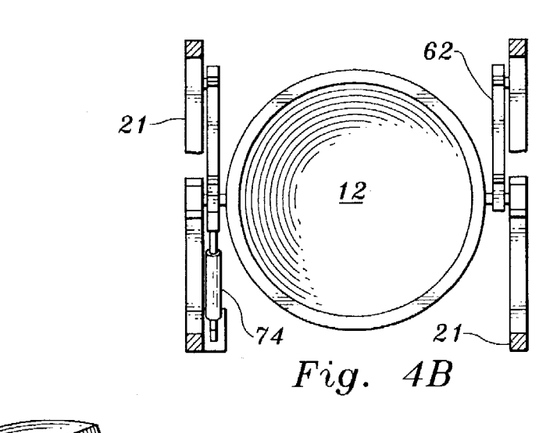
FIG. 4B is a front elevation view of the waste receptacle of FIG. 4A and associated components.
Figure 4C:
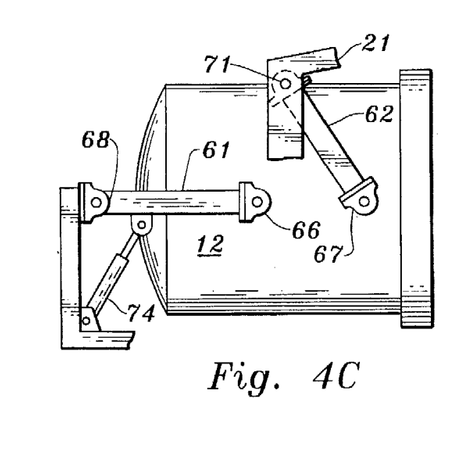
FIG. 4C is a side view of the waste receptacle and associated components.
Figure 4D:
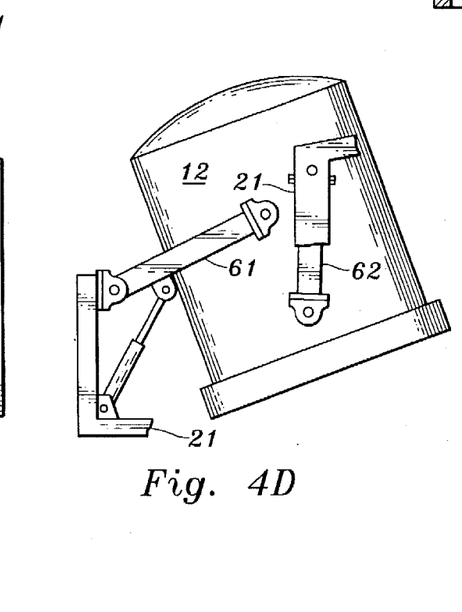
FIG. 4D is a side view of the apparatus of FIGS. 4A to 4C is it appears when the receptacle is pivoted to a dumping orientation.
Figure 4E:
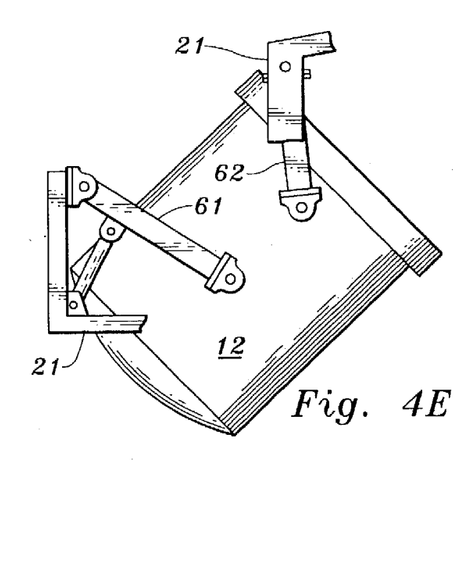
FIG. 4E is a side view of the apparatus of FIGS. 4A to 4D as it appears when the receptacle is pivoted to a loading orientation.

The locations of the first and second pivot couplings 66 and 67 are midway between the portions of the receptacle 12 that are uppermost and lowermost when the receptacle is at the horizontal orientation shown in FIG. 4C. At that orientation of the receptacle 12 the first pivot arms 61 are horizontal and extend towards the back end of the receptacle. Second pivot arms 62 extend upward and away from the front of the receptacle 12, preferably at an angle of about 30° from vertical, when the receptacle is at that orientation. Third pivot couplings 68 couple the back ends of first pivot arms to an adjacent portion of the movable frame 21 and establish a third pivot axis 69 which is parallel to the first and second pivot axes. Fourth pivot couplings 71 couple the upper ends of second pivot arms 62 to another portion of the frame 21 and establish a fourth pivot axis 72 that is parallel to the other pivot axes.

The first pivot arms 61 are constrained to pivot synchronously by a torque transfer cylinder 73 that extends between the back ends of the arms in coaxial relationship with the third pivot axis 69. Pivoting of the receptacle 12 about the first and second pivot axes 63 and 64, accompanied by raising or lowering of the receptacle as a whole, is effected by another extensible and contractible actuator 74 coupled between one of the first pivot arms 61 and movable frame 21. Extension of the actuator 74 swings the first pivot arms 61 upward from the horizontal orientation shown in FIG. 4C. The second pivot arms 62 concurrently force the receptacle 12 to turn about the second pivot axis 64 and thereby bring the receptacle into the dumping orientation shown in FIG. 4D. Contraction of actuator 74 swings the first pivot arms 61 downward from the horizontal orientation shown in FIG. 4C. Second pivot arms 62 concurrently force the receptacle 12 to turn about second pivot axis 64 thereby bringing the receptacle to the loading orientation shown in FIG. 4E.

The apparatus can have only a single first pivot arm 61 and second pivot arm 62 which need not necessarily be at the same side of the receptacle 12 if the associated pivot couplings have sufficient structural strength to support the receptacle in a cantilevered manner. In some variations of the apparatus the actuator 74 can be coupled between the frame and one of the second pivot arms 62. If, for example, in a system where the receptacle only needs to pivot between a horizontal orientation as shown in FIG. 4C and a dumping orientation shown in FIG. 4E then the actuator can be coupled to one of the second pivot arms 62 if the location of the first pivot couplings 66 is slightly lower than is depicted in FIG. 4C.

Figure 5:
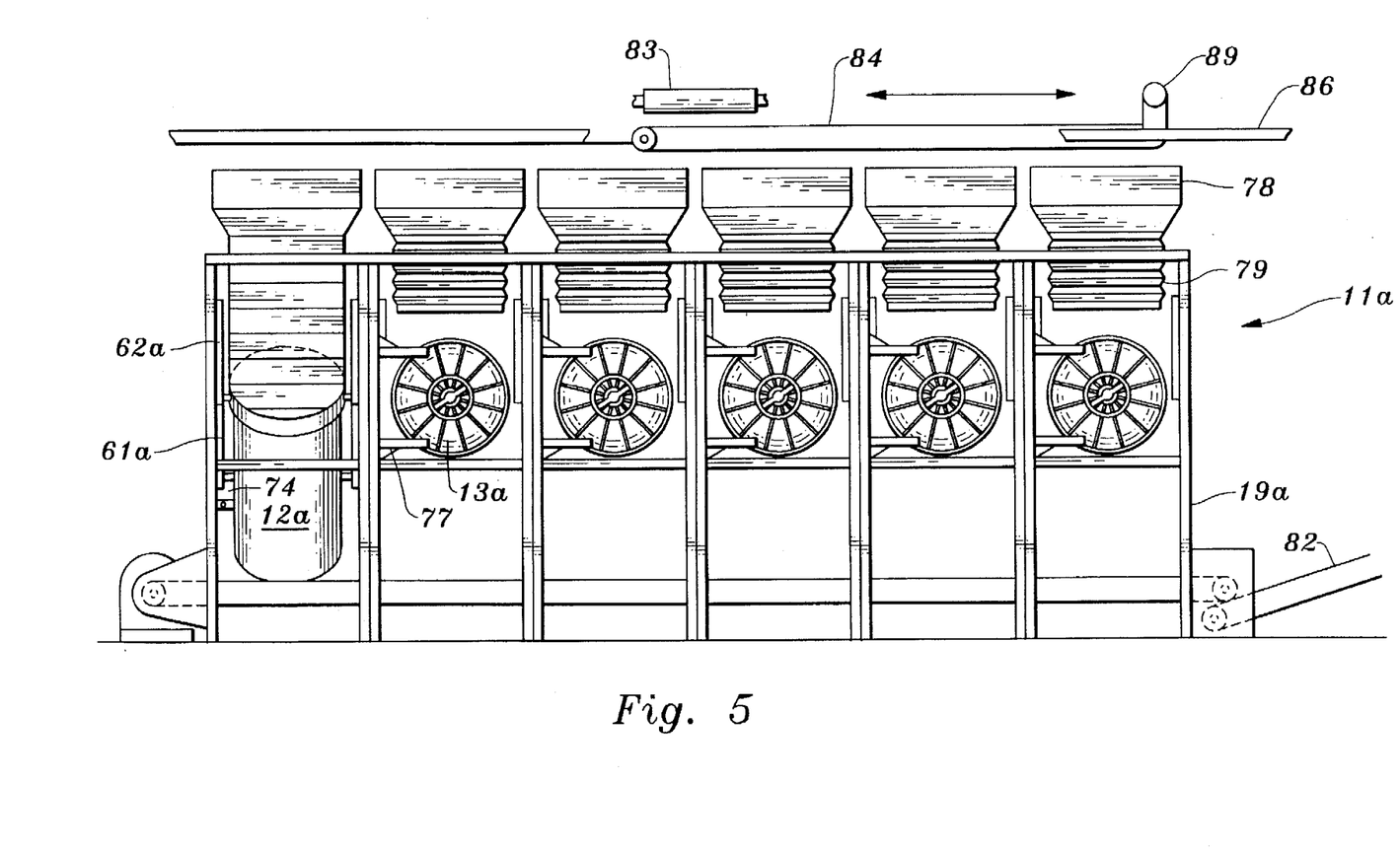
FIG. 5 is a front elevation view of waste sterilizing installation in accordance with a second embodiement of the invention.
Figure 6:
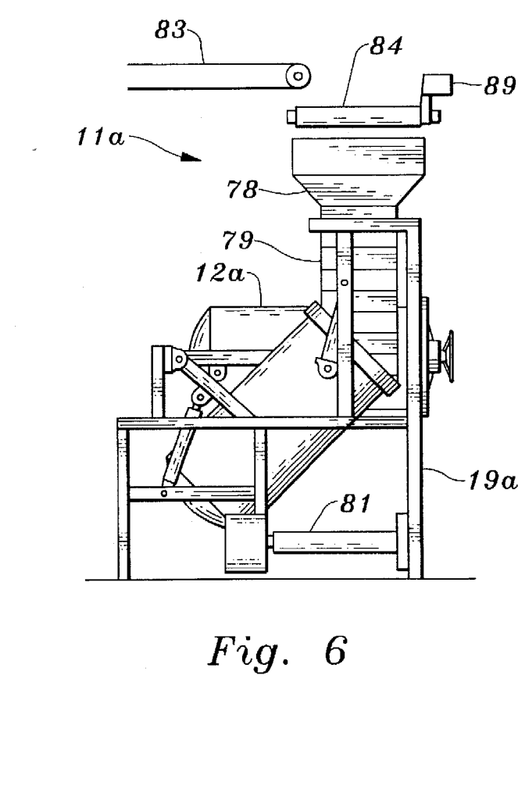
FIG. 6 is a side elevation view of the waste sterilizing installation of FIG. 5.

The receptacle 12 support and positioning mechanism described above is not limited to use in sterilizing apparatus which has an internal compactor and in which the receptacle is carried by a movable framework. For example, FIGS. 5 and 6 depict a high capacity installation 11a which can receive and sterilize wastes on a continuous process basis. The installation 11a has an extended fixed framework 19a which supports a series of waste receptacles 12a disposed in side-by-side relationship. Each such receptacle is supported by pairs of first and second pivot arms 61a and 62a which are pivoted by actuators 74 coupled between the framework 19a and the first pivot arms. The receptacles 12a, pivot arms 61a and 62a and associated pivot couplings may be similar to the corresponding components of the first described embodiment of the invention. Thus the receptacles 12a may each be separately pivoted between an upwardly directed loading orientation and a downwardly directed dumping orientation.

One of a series of pressure sealing doors 13a of the previously described kind is attached to the framework 19a in front of each receptacle 12a by hinges 77 in position to close and seal the receptacle when it is turned to a horizontal orientation.

One of a series of feed hoppers 78 is situated above each receptacle 12a in spaced apart relationship with the receptacle. One of a series of extensible and retractable tubular feed chutes 79 is secured to the underside of each hopper 78 and can be extended down into the hopper when it is at the loading orientation to direct wastes from the hopper into the receptacle. The chutes 79 are extended and retracted manually in this example but powered mechanism can be provided for the purpose if desired.

A motor driven conveyer belt 81 extends beneath the row of receptacles 12a to receive processed wastes that are dumped from the receptacles. Belt 81 deposits the wastes onto another motor driven conveyer belt 82 which inclines upward to carry the wastes to a compactor, truck or other destination.

The installation 11a does not necessarily require a separate conveyer belt to feed wastes to each hopper 78. A single motor driven feed conveyer belt 83 at the top of the installation 11a may be used to deposit the incoming wastes on a translatable conveyer 84 which is situated above the hoppers 78. In the preferred form the feed conveyer belt 83 deposits the waste on translatable conveyer 84 at a location which is midway between the ends of the line of hoppers 78. The translatable conveyer belt 84 is driven by a reversible drive motor 79 and has a length slightly longer than one half of the length of the line of hoppers 78. The translatable conveyer belt 84 may be traveled along a pair of support rails 86 which extend in parallel relationship with the line of hoppers 78 to locations at which the waste discharging end of the belt 84 is over any selected one of the hoppers.

Thus the installation 11a may receive incoming wastes in one hopper 78 while one or more other hoppers are turned away from the loading orientation to provide for sterilizing and/or dumping of previously received wastes. The installation 11a may be provided with a sufficient number of receptacles 12a to enable processing of a continuous inflow of wastes.

While the invention has been disclosed with respect to certain specific embodiments for purposes of example, many variations and modifications of the apparatus are possible and it is not intended to limit the invention except as defined by the following claims.

I claim:

1. A waste sterilizer having a framework and a receptacle supported thereby in which wastes are sterilized which receptacle has an opening for receiving wastes and wherein the receptacle is pivotable between a loading orientation at which wastes are retained in the receptacle and a waste dumping orientation at which wastes are released from the receptacle through the opening, wherein the improvement comprises:

said receptacle being coupled to said framework by at least a first pivot arm and a second pivot arm each of which is pivotable relative to the framework and pivotable relative to the receptacle, the first pivot arm being coupled to a side of the receptacle by a first pivot coupling having a first horizontally directed pivot axis and the second pivot arm being coupled to the side of the receptacle by a second pivot coupling having a second horizontally directed pivot axis, said second pivot coupling and second horizontally directed pivot axis being closer to said opening than the first pivot coupling and first horizontally directed pivot axis.

2. The apparatus of claim 1 wherein the first pivot arm is coupled to the framework by a third pivot coupling and the second pivot arm is coupled to the framework by a fourth pivot coupling which is horizontally and vertically spaced apart from said third pivot coupling.

3. The apparatus of claim 2 wherein said receptacle is pivotable into a horizontal orientation at which said opening faces in a horizontal direction and wherein said first and second and third pivot couplings are located to be in alignment with each other when said receptacle is at said horizontal orientation, said fourth pivot coupling being vertically spaced apart from said second pivot coupling and being further from said opening than said second pivot coupling when said receptacle at said horizontal orientation.

4. The apparatus of claim 2 wherein said receptacle is pivotable into a horizontal orientation at which said opening faces in a horizontal direction and wherein said first and second pivot couplings are located substantially midway between portions of said receptacle that are uppermost and lowermost when the receptacle is at said horizontal orientation.

5. The apparatus of claim 1 further including at least one extendible and contractible actuator, a fifth pivot coupling connecting one end of said actuator to said framework and a sixth pivot coupling connecting another end of said actuator to one of said pivot arms and wherein said first, second, third, fourth, fifth and sixth pivot couplings all have parallel pivot axes.

6. The apparatus of claim 5 wherein said actuator has a stroke sufficient to turn said receptacle between a loading orientation at which said opening faces at least partially in an upward direction and a dumping orientation at which said opening faces at least partially in a downward direction.

7. The apparatus of claim 1 wherein said receptacle is coupled to said framework by a pair of first pivot arms situated at opposite sides of the receptacle and a pair of second pivot arms situated at opposite sides of the receptacle, the first pivot arms being coupled to the receptacle by a pair of first pivot couplings having colinear pivot axes and the pair of second pivot arms being coupled to the receptacle by a pair of second pivot couplings having colinear pivot axes, the first pivot arms being coupled to said framework by a pair of third pivot couplings having colinear pivot axes and the second pivot arms being coupled to said framework by a pair of fourth pivot couplings having colinear pivot axes.

8. The apparatus of claim 1 wherein said framework is a movable framework, further including a fixed framework supporting said movable framework, said movable framework being translatable along said fixed framework in a horizontal direction between a waste sterilizing position and a loading and dumping position.

9. The apparatus of claim 8 further including a door proportioned for closing said opening of said receptacle, said door being attached to said fixed framework and being movable towards said opening and away therefrom at said waste sterilizing position of said receptacle.

10. The apparatus of claim 9 further including a plurality of door support rods extending outward from said movable framework at locations adjacent to said loading position of said movable framework and a plurality of collars each being engaged on a separate one of said rods and being slidable therealong in a direction at right angles to the path of travel of said movable framework and receptacle, said door being secured to said sleeves.

11. The apparatus of claim 8 further including a pair of spaced apart parallel rails extending in the direction of travel of said movable framework between said positions thereof, further including a plurality of roller wheels secured to said movable framework and riding on said rails.

12. The apparatus of claim 8 further including a waste compactor having an open topped and open ended compactor chamber which extends below said loading and dumping position of said movable framework and having a translatable ram which extends below said waste sterilizing position and which is translatable to force processed wastes out of an end of said compactor chamber.

13. The apparatus of claim 8 further including a conveyer belt extending below said loading and dumping position of said movable framework.

14. The apparatus of claim 1 wherein said framework is a movable framework, further including:
 a fixed framework supporting said movable framework and receptacle,
 a pair of horizontally extending spaced apart parallel rails secured to said fixed framework and defining a path of travel of said movable framework and receptacle between a loading position thereof and a dumping position thereof,
 a plurality of roller wheels secured to said movable framework and riding on said rails,
 a door supported by said fixed framework and being movable towards said opening of said receptacle and away therefrom at said loading position thereof, said door being proportioned to open and close said opening when said movable frame and receptacle are at said waste sterilizing position,
 a first extendible and contractible actuator having an end connected to said fixed framework and another end connected to said movable framework which first actuator extends in parallel relationship with said rails, and
 a second extendible and contractible actuator having one end connected to said movable framework in a pivotal manner and another end connected to one of said pivot arms in a pivotal manner.

15. The apparatus of claim 1 having a plurality of said receptacles disposed in side by side relationship and a plurality of said first pivot arms and a plurality of said second pivot arms, each of said receptacles being coupled to said framework by a separate pair of said first pivot arms and a separate pair of said second pivot arms, wherein said apparatus further includes:
 a plurality of extendible and contractible actuators each having one end pivotally connected to said framework and another end pivotally coupled to a first pivot arm at a separate one of the receptacles, said actuators having a stroke sufficiently long to turn said receptacles between loading orientations at which the openings of the receptacles face at least partially in an upward direction and dumping orientations at which the openings face at least partially downward,
 a plurality of doors attached to said framework each being adjacent a separate one of said receptacles and being movable towards the adjacent one of the receptacles and being movable away therefrom to close and open the opening of the adjacent receptacle when the receptacle is at an intermediate orientation at which the opening of the receptacle faces in a horizontal direction.

16. The apparatus of claim 15 further including a plurality of waste receiving hoppers each being disposed above a separate one of said receptacles in spaced apart relationship therewith and a plurality of waste guiding chutes each extending between a separate one of said hoppers and the underlying one of said receptacles, said waste guiding chutes being extendible towards said receptacles and retractable away therefrom.

17. The apparatus of claim 16 further including a motor driven conveyer belt disposed below said receptacles in spaced apart relationship therewith.

18. A waste sterilizer comprising:
 a framework;
 a receptacle forming a sterilization chamber and having opposites sides and front and back ends and an opening at the front end for enabling entry of wastes into said chamber and release of wastes therefrom;
 a pair of first pivot arms which are disposed at opposite sides of the receptacle;
 a pair of second pivot arms which are disposed at the opposite sides of the receptacle;
 a pair of first pivot couplings each coupling a separate one of said first pivot arms to said receptacle, said first pivot couplings being pivotable about a first horizontally directed pivot axis which is spaced apart from said front and back ends of the receptacle;
 a pair of second pivot couplings each coupling a separate one of said second pivot arms to said receptacle, said second pivot couplings being pivotable about a second pivot axis which is parallel to said first pivot axis and which is closer to said front end of said receptacle than said first pivot axis;
 a pair of third pivot couplings coupling said first pivot arms to said framework, said third pivot couplings being pivotable about a third pivot axis which is parallel to said first horizontally directed pivot axis;

a pair of fourth pivot couplings coupling said second pivot arms to said framework, said fourth pivot arms being pivotable about a fourth pivot axis which is parallel to said first horizontally directed pivot axis and which is horizontally and vertically spaced apart from said third pivot axis;

an actuator coupled to at least one of said first pivot arms for pivoting the arm about said third pivot axis; and a door supported by said framework and being movable towards said receptacle and away therefrom, said door being proportioned to close said opening when said receptacle is pivoted into an orientation at which said opening faces in a horizontal direction.

19. The apparatus of claim 18 wherein said framework is a movable framework that is translatable in a horizontal direction between a sterilizing position at which said receptacle opening faces said door and a loading and dumping position at which said opening is away from the location of said door, said apparatus having a fixed framework and a pair of parallel horizontally extending rails secured thereto and which support said movable framework.

20. The apparatus of claim 19 further including a waste compactor, said compactor having an open topped and open ended compactor chamber which extends beneath said loading and dumping position of said receptacle and having a translatable ram which extends beneath said sterilizing position of said receptacle and which is movable along the compactor chamber to force processed wastes out of an open end of the chamber.

* * * * *